United States Patent [19]

Horrobin et al.

[11] Patent Number: 5,216,142
[45] Date of Patent: Jun. 1, 1993

[54] ANTI-VIRALS

[75] Inventors: David F. Horrobin; John C. M. Stewart; Michael D. Winther, all of Guildford, England

[73] Assignee: Efamol Holdings plc, Surrey, England

[21] Appl. No.: 521,075

[22] Filed: Apr. 10, 1990

[30] Foreign Application Priority Data

Apr. 17, 1989 [GB] United Kingdom ............... 8908646
Sep. 20, 1989 [GB] United Kingdom ............... 8921266

[51] Int. Cl.$^5$ .................. C07H 17/00; A61K 31/70
[52] U.S. Cl. ........................... 514/50; 514/43; 514/46; 514/49; 514/262; 544/265; 536/28.2
[58] Field of Search ............ 536/23; 514/43, 46, 514/49, 262; 544/265

[56] References Cited

U.S. PATENT DOCUMENTS 4,797,479 1/1989 Shuto et al. ..................... 536/27
4,921,951 5/1990 Shuto et al. ..................... 536/27

FOREIGN PATENT DOCUMENTS

| 0056265 | 7/1982 | European Pat. Off. . |
| 082668 | 6/1983 | European Pat. Off. . |
| 0085424 | 8/1983 | European Pat. Off. . |
| 0130126 | 1/1985 | European Pat. Off. . |
| 0199451 | 10/1986 | European Pat. Off. . |
| 0217580 | 4/1987 | European Pat. Off. . |
| 2066812 | 7/1981 | United Kingdom . |
| 89/03837 | 5/1989 | World Int. Prop. O. . |
| 89/03838 | 5/1989 | World Int. Prop. O. . |

OTHER PUBLICATIONS

Journal of Medicinal Chemistry vol. 19, No. 5 May 1976 Moffatt et al 2-Acyloxyisobutyryl halides pp. 667–673.
Journal of Medicinal Chemistry, 1976, vol. 19 No. 5, Moffatt et al 2-Acyloxyisobutyryl halides pp. 654–662.
Journal of Medicinal Chemistry vol. 19, No. 5 May 1976 Moffatt et al 2-Acyloxyisobutyral Halides pp. 663–667.
Chemical Abstracts vol. 85 No. 25 Dec. 1976 p. 585 Abstract No. 193040z. U.S. & JP-A-76 32 573 Mar. 1976.
Chemical Abstracts, vol. 105, No. 11, Sep. 1986 p. 678 Abstract No. 97876n, US & JP-A-61 44 897 Mar. 1986.
Chemical Abstracts vol. 98, No. 25 Jun. 1983, p. 437, Abstract No. 214136w, US; & JP-A-58 13 394, Jan. 1983.
Chemical Abstracts, vol. 76, No. 7 Feb. 1972, p. 345 Abstract No. 34533k, US & JP-A-71 37 827 Nov. 1971.
Medical Hypotheses (1990) 32, 211–217 Horrobin "Post Viral Fatigue Syndrome, Viral Infections in Atopic Eczema and Essential Fatty Acids".
Journal of Nutritional Medicine (1990) 1, 145–151 Horrobin "Essential Fatty Acids, Imunity and Viral Infections".
Chemical Abstracts, vol. 85, No. 15, Oct. 1976, p. 494 Abstract No. 108943d, U.S. & JP-A-76 26 833 Mar. 1976.
M. MacCross, et al., Biochem and Biophys Res. Comm. 85(2):714–723, 1978.

Primary Examiner—John W. Rollins
Attorney, Agent, or Firm—Nixon & Vanderhye

[57] ABSTRACT

Anti-virals wherein a linoleyl, gamma-linolenyl or other unsaturated long chain fatty acyl group is borne directly on a hydroxy or amino group of the sugar/sugar analogue or heterocyclic moiety of a nucleoside or nucleoside analogue.

18 Claims, No Drawings

ANTI-VIRALS

FIELD OF INVENTION

The invention relates to anti-viral agents; they are fatty acid nucleosides and nucleoside analogue derivatives, and corresponding compounds with the fatty acid groups carried on an amino rather than hydroxy function of the nucleoside or nucleoside analogue.

GENERAL

A number of compounds have been shown to exert anti-viral actions both in vitro and in vivo, in particular various purine and pyrimidine derivatives with a glycoside or glycoside analogue structure. Examples include:

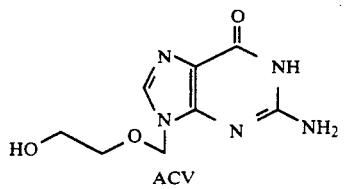

ACV
(acyclovir; 9-(2-hydroxyethoxymethyl)guanine)

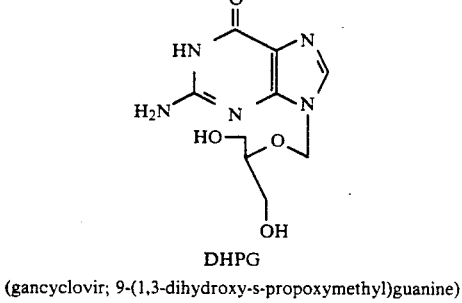

DHPG
(gancyclovir; 9-(1,3-dihydroxy-s-propoxymethyl)guanine)

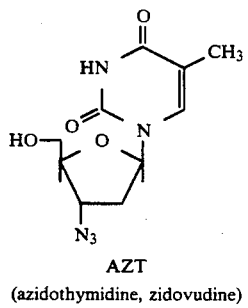

AZT
(azidothymidine, zidovudine)

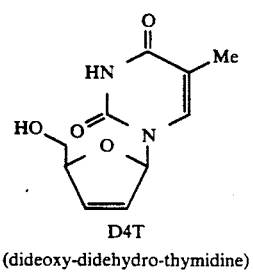

D4T
(dideoxy-didehydro-thymidine)

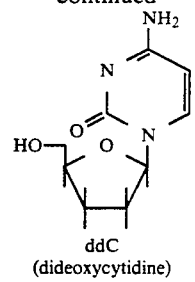

ddC
(dideoxycytidine)

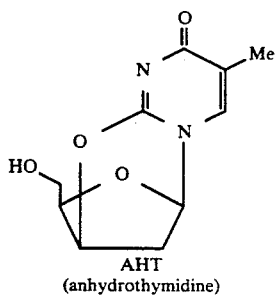

AHT
(anhydrothymidine)

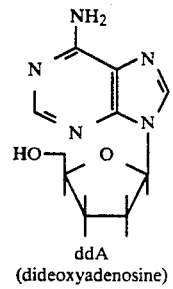

ddA
(dideoxyadenosine)

In use, all these compounds, which are analogues of natural nucleosides, have limited ranges of action and even in vitro they affect only a limited range of viruses. Their mode of action is primarily to interfere with one or other of the stages of viral replication and assembly, an action referred to as replication inhibition herein. They do not inactivate the virus when it is present extra-cellularly and they have little or no effect on the transmission of active virus from cell to cell.

There are agents of a different kind that are able to inactivate viruses and inhibit their transmission, especially those viruses which are enveloped. These agents include long chain unsaturated fatty acids and their derivatives such as esters, salts, amides and glycerides. The effects of these agents are referred to as virus inactivation herein, but there may also be limited inhibitory effects on replication. It is thought that a major component of the virus inactivation is simply the result of the dramatic disruption of the protecting virus envelope.

THE INVENTION

The invention has several distinct but overlapping and inter-related aspects described primarily in relation to AZT, AHT and acyclovir derivatives but extending equally to ddC, ddA, D4T and gancyclovir derivatives.

At its broadest the invention provides new antiviral compounds, being long chain, unsaturated fatty acid ester or amide derivatives of nucleosides and nucleoside analogues, the fatty acid acyl groups being borne directly on a hydroxy or amino group of the sugar/sugar-analogue or heterocyclic moiety of the nucleoside or nucleoside analogue. The fatty acids are C:16 upwards, preferably polyunsaturated, and are conveniently linoleyl, gamma-linolenyl or other unsaturated long chain fatty acyl groups of the natural n-9 and n-7 series (C:16 upwards) or n-6 and n-3 series (C:18 upwards). Particular examples of the nucleoside analogues are AZT and AHT, and ACV.

The invention in the present aspect also provides:

(i) A method of enhancing transport of anti-virals across lipid barriers in the body, and especially from the gut into the lymph system, or into cells from the extracellular fluid, or across the blood brain barrier, or percutaneously in topical preparations, or of inhibiting glucuronidation or other metabolic modifications reducing drug efficacy, in the treatment of viral infections, wherein said anti-viral is used in the form of a compound as above.

(ii) A method of preparation of a medicament for such purposes, wherein a compound as above is prepared as said medicament alone or in a pharmaceutically acceptable diluent or carrier.

In a second aspect the invention provides compounds being derivatives of pentose nucleosides, or of analogues thereof having an acyclic group in place of the pentose which acyclic group has a hydroxy substituted carbon at the position corresponding to the 5' position of the pentose, said derivatives being esters at the 5' position of the nucleoside or at the corresponding hydroxy substituted carbon of the analogue as the case may be, formed with the fatty acids referred to above and particularly with linoleic acid, gamma-linolenic acid, or other unsaturated long chain fatty acids of the n-9 and n-7 series (C:16 upwards) and n-6 and n-3 series (C:18 upwards).

Especially in the present aspect the invention provides AZT or AHT, or ACV, or ddA, ddC or D4T in the form of such compounds.

The invention in this aspect further provides:

(i) A method of treatment of viral infections, with enhancement or inhibition as above but without loss of replication inhibiting activity, wherein said anti-viral is used in the form of a compound that is such a 5' or corresponding ester derivative.

(ii) A method of preparation of a medicament for such purposes, wherein such a compound is prepared as said medicament alone or in a pharmaceutically acceptable diluent or carrier.

In a third aspect the invention provides AZT and AHT, or ddA, ddC or D4T in the form of an ester derivative of the fatty acids referred to above and particularly linoleic acid, gamma-linolenic acid, or other unsaturated long chain fatty acid of the n-6 and n-7 series (C:16 upwards) and n-6 and n-3 series (C:18 upwards), active against herpes or other virus infection.

The invention in the present aspect further provides:

(i) A method of treatment of herpes virus infection, particularly herpes simplex and herpes zoster or other sensitive viral infection, wherein there is administered to a sufferer therefrom an effective amount of such an AZT or AHT or ddA, ddC or D4T derivative.

(ii) Preparation of a medicament for the treatment of herpes virus infection, particularly herpes simplex and herpes zoster or other sensitive viral infection, wherein such an AZT or AHT or ddA, ddC or D4T derivative is prepared as said medicament, alone or in a pharmaceutically acceptable diluent or carrier.

In a fourth aspect the invention provides acyclovir or gancyclovir in the form of a virucidal ester or amide of a fatty acid as referred to above, again particularly of linoleic acid, gamma-linolenic acid, or other unsaturated long chain fatty acid of the n-9 and n-7 series (C:16 upwards) and n-6 and n-3 series (C:18 upwards).

In this aspect the invention further provides:

(i) A method of treatment of virus infection wherein there is administered to a sufferer therefrom an effective amount of such an acyclovir or gangcyclovir derivative.

(ii) Preparation of a medicament for the treatment of virus infection, wherein such an acyclovir or gancyclovir derivative is prepared as said medicament alone or in a pharmaceutically acceptable diluent or carrier.

(iii) Such method, or preparation of medicament, wherein the infection is herpes simplex or herpes zoster or other sensitive viral infection.

Specific aspects of the invention may also be stated as lying in:

(i) Particular derivatives of particular nucleoside analogue anti-virals, namely esters of AZT and AHT with long chain unsaturated fatty acids of the n-9 etc. series set out herein. These are believed to be new compounds, but the invention is more specifically in their application against herpes viruses, including herpes zoster and herpes simplex, where AZT and AHT are inactive. In this aspect therefore the invention lies in treating herpes infections with these esters, or in the preparation for such treatment of medicaments containing the esters.

ii) Particular derivatives of a particular nucleoside analogue anti-viral; namely esters or amides of acyclovir with long chain unsaturated fatty acids of the n-9 etc. series set out herein.

The formula of GLA-acyclovir ester is, for example:

where the pentose ring of AZT or AHT is represented by equivalents to the 1', 4' and 5'-carbon atoms of the ring. GLA-acyclovir amide carries the gamma-linoleoyl group on the amino substituent of the purine nucleous, and di-GLA-acyclovir at both positions.

These are again believed to be new compounds, but the invention also lies in treating virus infections, especially herpes virus infections with them, and in the preparation for use in such treatment of medicaments containing the esters.

DISCUSSION

The fatty acid nucleoside derivatives have dramatically different physico-chemical properties from the parent nucleoside compounds. The compounds of the present invention are lipophilic with high absolute solubilities in chloroform and a large chloroform-water partition co-efficient (see Tables 3 and 4 herein).

The fatty acid nucleoside derivatives have one or more of the following advantages that are a consequence of new physical and biological properties:

1. Combined virucidal and replication inhibition activities.

2. Broadening activity of replication inhibition to different viruses.

3. Enhanced penetration through and into the skin and into cells (topical formulations).

4. Improved pharmacokinetics (particularly in oral and i.v. formulations).

These advantages are discussed in greater detail below.

1. Combined virucidal and replication inhibition activities

The observation that two distinct modes of action against viruses can be combined in a single molecule and are shown by most of the compounds of the invention is unexpected. Although free long chain unsaturated fatty acids are virucidal to most enveloped viruses, triglycerides are not, so clearly some chemical linkages interfere with this type of activity, LA in triglyceride format for example fails to retain the virucidal activity of the fatty acid component.

The acyclovir esters with GLA or LA (AK5 and 6) are also lacking in this activity, but AKs 1, 2, 3, 4, 10, 11, 12 and 13 are all virucidal.

The second unexpected property of the compounds is that they retain the replication inhibiting activity of the parent nucleoside when tested in vitro assays for virus replication. This is surprising as many of the derivatives are 5'-hydroxy esters. For AZT and ACV it has been shown that the intra-cellular biologically active form is triphosphorylated at the 5'-hydroxy position. AZT and ACV, if tested lacking the phosphate groups, are inactive against viral polymerases.

There are two possible explanations as to the mode of action of the 5'-substituted compounds. The most likely is that the fatty acid group, having served its purpose in enhancing drug penetration through membranes, is rapidly cleaved off from the nucleoside by any of a variety of enzymes present in the cell cytoplasm. The de-acylated compound could then be a substrate for the phosphorylation needed to generate the active compound.

Less likely is the possibility that the fatty acid group in some way substitutes for the phosphorylation in the fatty acid-nucleoside, resulting in a compound which is active without cleavage and phosphorylation.

Results from anti-viral screening work are given later herein, and what stands out most clearly is that "AK 10" and "AK 11" (the di-substituted ACV compounds) are very effective both at inactivating virus and inhibiting replication. A 1 mg/liter solution of the compound AK 10 will inactivate 1 log (i.e. 90%) of virus and reduce virus replication by 1 log (90%).

2. Broadening activity against viruses

A further unexpected observation is that, for example, GLA-AZT gains the property of inhibiting herpes virus replication, a property not found with either GLA or AZT individually (Table 5 herein). The precise basis for this broadening of activity of an anti-retroviral agent to include herpes viruses is unknown but could be due to the enhanced permeability through cell membranes. Since multiple concomitant viral infections frequently occur it is of potential clinical benefit to treat them with a single active compound.

3. Enhanced penetration through skin

Topical treatments for herpes virus infections were the first formulations to be developed for this virus. However, all such formulations produced to date have been of limited value for two reasons: firstly because the anti-viral agents are not lipophilic they do not easily penetrate the skin and therefore do not always achieve therapeutic concentrations at the site of virus replication. For this reason agents known as "enhancers" (e.g. dimethyl sulphoxide and propylene glycol) have been added to improve percutaneous absorption. However, most enhancers cause local toxicity and irritation with prolonged use. Thus lipophilic derivatives of anti-virals that retain all of their potency in inhibiting virus replication are desirable.

The second reason for the disappointing results obtained with known topical treatments is that the virus replication occurs early in the natural history of infection, at the prodromal stage, usually before lesions are apparent. Thus any agent that acts only on the viral polymerase will be unable to halt further development of the lesion. However, an agent with virucidal properties, capable of disrupting the envelope structure of intact virus, may be expected to have superior efficacy in halting lesion development, reducing the change of spreading infections virus to new locations and possibly reducing the subsequent load of latent virus that will lead to subsequent infections.

The compounds of the present invention, particularly AKs 10, 11, 12 and 13 are virucidal and are lipophilic so their penetration through the lipid matrix of the stratum corneum and also their penetration into cells will be efficient. These compounds will be present in the oil phase of oil-in-water or water-in-oil emulsions which simplifies the manufacture and application of such products.

4. Improved pharmacokinetics

The metabolism and pharmacokinetics of fatty acid nucleosides are dramatically altered compared to the parent nucleosides. Some examples of how this will enhance the therapeutic efficacy are given.

a. Drug absorption

The lipid solubility of a drug is fundamental to absorption. For polar compounds (those which dissolve more easily in water than lipid) such as the parent nucleosides, crossing a non-porous, lipid membrane by diffusion is difficult and hence this process becomes rate limiting. Lipid soluble agents pass more easily through the barrier membranes of the gastro-intestinal tract which will increase their oral bioavailability. They will also tend to be absorbed at least in part by the lymphatic system. This latter route has the considerable advantage of avoiding the liver whereas water soluble agents are absorbed via the portal vein and so must go through the liver before reaching the general circulation. The "first pass metabolism" encountered during transport through the liver is a principal route of drug modification leading to excretion of inactive metabolites.

It is known that saturated fatty acids can enhance the transport of drugs across membranes but this has been believed efficient only with the shorter chain molecules of 6-12 carbons in length (for example see "Drug Delivery and Targeting Systems", 30.11.90. to 1.12.89. London, Conference documentation IBC Technical Services Ltd. Article by Professor Y. W. Chien). From this data it would have been expected that the longer chain unsaturated fatty acids of the present invention would be less effective, not active as they are.

b. Blood brain barrier

Many viruses (such as HIV and certain herpes viruses) are able to spread to the brain and cause infections leading to encephalitis or dementia. A critical factor in treatment is then the ability of a drug to pass through the blood brain barrier. It has been repeatedly observed that hydrophilic drugs do not readily pass the blood brain barrier and so only low levels can be detected in cerebrospinal fluid. Lipophilic drugs will more easily reach therapeutic levels in the brain. This is especially the case for the compounds of the present invention when given by the i.v. route.

c. Altered metabolism

Fifteen to twenty percent of zidovudine (AZT) is excreted unchanged into the urine and seventy five percent is metabolised by hepatic glucuronidation to form 3'-azido-2'-3'-dideoxy-5'-glucuronyl thymidine (an inert metabolite). Since derivatives such as AK1 (GLA-AZT) and AK2 (LA-AZT) have an ester linkage at this 5' position these will not be metabolised by the same pathway. This will increase the effective blood concentration and allow a lower does of drug to achieve the same therapeutic benefit.

The combination of higher bioavailability and reduced metabolism will result in less variation in pharmacokinetics between individuals and so lead to lower doses and reduced incidence of toxic side effects.

There are further advantages to the production of amide derivatives of the anti-viral agents ddC and ddA. For both drugs the combined ester and amide linkages will increase lipophilicity and even if one of the fatty acids were to be removed by enzymic metabolism the remaining molecule will still be lipophilic and retain the advantages described.

For amide derivatives of ddA there is a further specific advantage in that this linkage will prevent the conversion of ddA to ddI (dideoxyinosine) following deaminiation by adenosine deaminase which occurs within minutes of exposure to human plasma. If the fatty acid-dda derivative can enter an HIV infected cell it can be converted to dda and subsequently to the active triphosphate form. In contrast ddI must eventually undergo further enzymic conversions to form ddA triphosphate (the active metabolite within the cell.

Furthermore, in order to be fully effective, most anti-viral agents must be present in both intracellular and extra-cellular compartments. Since the cell membrane is lipid rich, lipophilic compounds are more readily able to enter cells than are hydrophilic ones. Thus the drugs specified in the present invention are most likely to achieve effective intra-cellular concentrations than are their parent compounds.

SUITABLE FATTY ACIDS AND SOURCES

Suitable unsaturated fatty acids include the natural n-7, n-9, n-6 and n-3 series fatty acids, the members of which up to C:22 are included in Table 1 below:

TABLE 1

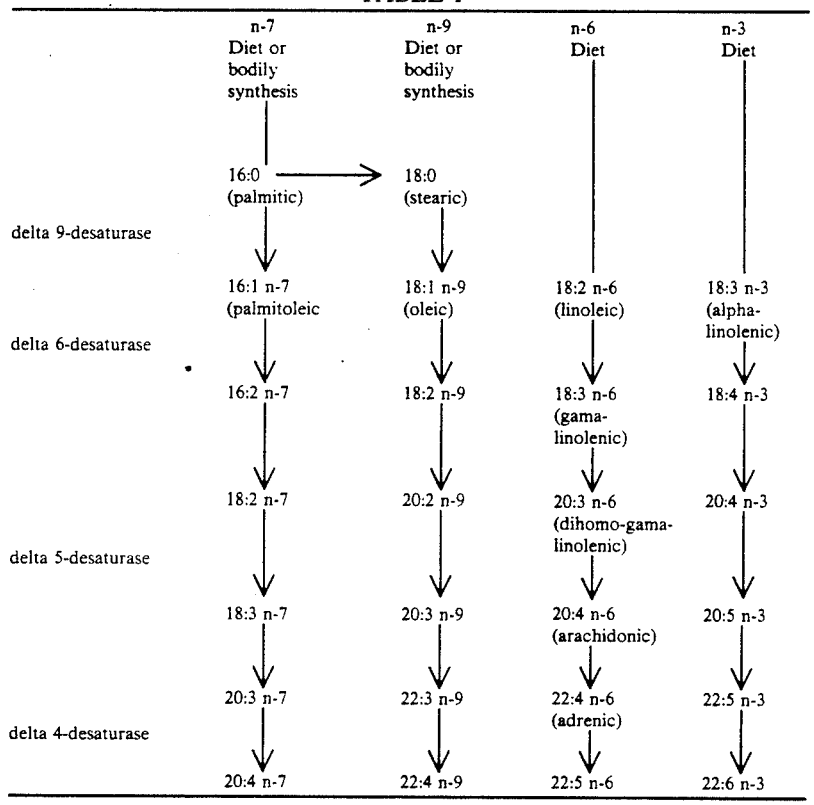

In the body the n-6 and n-3 series are dietary requirements, at least linoleic acid (LA) and alphalinolenic acid (ALA) therefore being required as essential fatty acids. The n-7 and n-9 series are available endogenously, from palmitic acid (16:0) and stearic acid (18:0) respectively, by the action of delta-9 desaturase and the successive action of the other desaturases. The palmitic and stearic acids may be from dietary sources or bodily synthesis.

The position of the double bonds under the n-7, n-9 etc. nomenclature is counted from the non-carboxyl or omega end, with the unsaturations present in the chain as ($-CH=CH-CH_2-$)$_M$, where M=1 to 6, as represented in the terminology 18:1, 22:3, etc. Illustrations are:

TABLE 2 n-6 series essential fatty acids

18:2 delta-9,12 (linoleic acid)
18:3 delta-6,9,12 (gamma-linolenic acid)

20:3 delta-8,11,14 (dihomo-gamma-linolenic acid)
20:4 delta-5,8,11,14 (arachidonic acid)
22:4 delta-7,10,13,16 (adrenic acid)
22:5 delta-4,6,10,13,16 n-3 series essential fatty acids

18:3 delta-9,12,15 (alpha-linolenic acid)
18:4 delta-6,9,12,15
20:4 delta-8,11,14,17
20:5 delta-5,8,11,14,17
22:5 delta-7,10,13,16,19
22:6 delta-4,7,10,13,16,19

The acids are systematically named as derivatives of the corresponding hexadecanoic, octadecanoic, eicosanoic or docosanoic acids, e.g. delta-9,12-octadecadienoic acid or delta 4,7,10,13,16,19-docosahexanenoic acid, but numerical designations such as, correspondingly, 18:2 n-6 or 22:6 n-3 are convenient. Initials, for example, AA for arachidonic acid and more systematically DHA for 22:6 n-3 (docosahexaenoic acid) or EPA for 20:5 n-3 (eicosapentaenoic acid), are also used but as to the latter kind do not serve when n-3 and n-6 acids of the same chain length and degree of unsaturation exist, as for example with the 22:5 acids. Trivial names in more or less common use in the n-6 series are as shown. Of the n-3 series only 18:3 n-3 has a commonly used trivial name, alpha-linolenic acid. It was characterised earlier than gamma-linolenic acid and reference in the literature simply to linolenic acid, especially in the earlier literature, is to the alpha-acid.

Fatty acids for use in the invention may be derived from natural sources, known in themselves and no part of the invention, or from chemical synthesis. For example oils derived from the seeds of certain plants such as *Oenothera biennis, Borago officinalis* and members of the Ribes family are often rich in 18:3 n-6. The oils from certain algae such as Spirulina spp and certain fungi such as Mortierella spp and Rhizopus spp may also contain 18:3 n-6. The 20:4 n-6 acid is found in egg yolks, in the lipids of certain fungi and algae, and in fish and other marine oils, especially those from warm waters. The 18:3 n-3 acid is widely distributed in plant oils, which 18:4 n-3 is found in the seed oils from members of the Ribes family. The 20:5 n-3 and 22:6 n-3 acids are often abundantly present in marine oils. Natural sources of 22:4 n-6 and 22:5 n-6 include adrenal glands (22:5 n-6) and kidneys (22:4 n-6) obtained from slaughter houses.

The n-9 fatty acid oleic acid (18:1 n-9) can be obtained from a large variety of plant oils, notably olive oil, and palmitoleic (16:1 n-7) can be found in most plant oils also.

DOSAGES

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The amounts of the compounds to be administered are 1 mg to 20 g per day in divided doses, preferably 10 mg to 4 g per day and more preferably 50 mg to 1 g per day and dosage unit forms are conveniently made up with these amounts or sub-multiples thereof. The compounds may be administered, orally, topically, enterally, parenterally (intravenously, intravascularly, intraperitoneally, intramuscularly or subcutaneously) or by any other appropriate route all per se known and using per se known presentations, though as already discussed herein there are advantages in particular modes of administration. This compounds may be administered as tablets, e.g. enteric-coated tablets to prevent destruction in the stomach, hard or soft gelatin capsules, syrups, emulsions, solutions, or any other form appropriate for oral or parenteral administration; or in any form appropriate for topical administration such as ointments, creams, shampoos, lotions; or as pessaries and other formulations for rectal or vaginal application, or sticks. When applied topically the products may be prepared in concentrations of the active compounds of from 0.001 to 20%, preferably 0.1 to 10%, and especially preferably 1 to 5% by weight. Such a preparation is desirably used to give, at most, the daily dosages above and desirably dosages at the lower end of the ranges for example 20 mg/day.

SYNTHESES

Example 1

GLA - 3'azido-3'-deoxythymidine, GLA-AZT ("AK 1") (Method A)

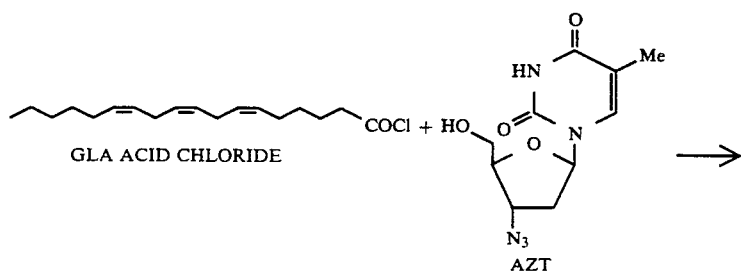

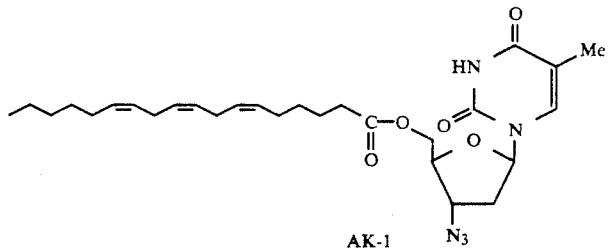

AK-1

Procedure: 1.05 mmol of AZT (IV 0.280 g) were dissolved in 3 ml of anhydrous pyridine and to this solution was added 1.15 mmol of GLA-acid chloride (III 0.340 g). The solution was stirred at 0° C. for one hour and then for period, the reaction mixture was evaporated to dryness to afford a syrup which was dissolved in dichloromethane (30 ml) and then washed with saturated sodium bicarbonate solution (20 ml). The organic layer was departed and evaporated in vacuo. The crude orange syrup was introduced onto the top of a 10 g column of silica gel. Elution with chloroform, followed by 20:1, 20:1, 10:1, $CHCl_3$ :MeOH mixtures enabled the separation of the required product (V). Yield = 391 mg, 71%.

The only difference with the other fatty acids is to use the corresponding acid chloride.

Example 2

GLA - Anhydrothymidine, GLA-AHT ("AK 3") (Method A)

period, TLC (thin layer chromatography) indicated complete loss of starting material and the pyridine was removed in vacuo, evaporation temperature being maintained below 45° C. The resulting crude syrup was dissolved in chloroform: petrol (2:1, v:v) and was introduced onto a column of silica gel (30 g) preequilibrated in chloroform: petrol (2:1) (be more specific as to the "petrol"). Elution with chloroform: petrol (2:1) removed the unwanted high r.f. (give r.f. in full) products. AK-1 was obtained as a colourless homogenous syrup by elution with chloroform: petrol (4:1). Yield 57% (0.77 g, 1.47 mmol).

Example 4

LA-AZT ("AK 2")

The procedure for this preparation is exactly as above. The quantities used were as follows: AZT, 0.723 g, 2.70 mmol. LA acid chloride, 1.3 g, 4.36 mmol. 10 ml of anhydrous pyridine. Yield, 54% (0.770 g, 1.458 mmol).

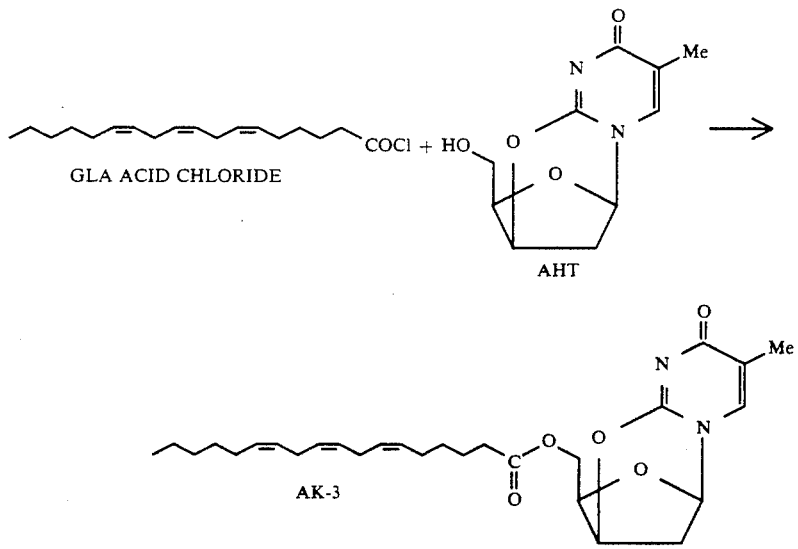

Procedure: As for GLA-AZT except that chromatography requires 10% MeOH; Yield of the title product VIII, 70%. As with GLA-AZT the only difference with other fatty acids is to use the corresponding acid chloride.

Example 3

GLA-AZT ("AK 1") (Method B)

To a stirred solution of AZT (0.684 g, 2.58 mmol, as a TLC-homogeneous gum) in anhydrous pyridine (10 ml), was added GLA acid chloride (1,200 g, 4.00 mmol). The reaction was stirred under dry nitrogen at room temperature for a period of six hours. After this

Example 5

GLA-AHT ("AK 3") (Method B)

Anhydrothymidine (0.520 g, 2.319 mmol, as a dry white powder) was dissolved in anhydrous pyridine (10 ml) under an atmosphere of dry nitrogen, and to this stirred solution at room temperature was added GLA acid chloride (0.900 g, 3.02 mmol). Stirring was continued overnight after which period, TLC indicated complete loss of the starting material. The pyridine was evaporated in vacuo (below 45° C.) and the residual syrup was dissolved in chloroform and then applied to a column of silica gel (30 g). Elution with chloroform-:petrol (4:1, v:v) followed by chloroform and then chloroform:ethanol (50:1) gave the required derivative AK-3 as a colourless TLC-homogeneous gum. Yield, 51% (0.573 g, 1.18 mmol).

EXAMPLE 6

LA-AHT ("AK 4")

The procedure for this preparation is exactly as above. The quantities used were as follows: AHT, 0.643 g, 2.86 mmol. LA acid chloride, 1.20 g, 4.00 mmol. 10 ml of anhydrous pyridine. Yield, 55% (0.765 g, 1.573 mmol).

EXAMPLE 7

Di-GLA-ACV ("AK 10") (Method A)

Acyclovir (0.85 g) was suspended in a stirred solution of pyridine (30 ml) and gamma-linolenyl chloride (2.5 g) slowly added to the pyridine. Acyclovir, which itself is insoluble in pyridine, gradually solubilises as gamma-linolenyl esters are formed. The solution was stirred overnight and then poured into 200 ml of saturated sodium bicarbonate solution. The sodium bicarbonate solution was extracted twice with 150 ml chloroform. The chloroform fraction was dried with anhydrous sodium sulphate and then evaporated to dryness under vacuum. The resulting gum was applied to a silica gel column (200 mesh) in hexane and chromatographed with hexane/chloroform in increasing chloroform proportions, to give after evaporation digamma-linolenyl acyclovir.

The only difference with the other fatty acids is to use the corresponding acid chloride, for example that of EPA, LA or AA.

EXAMPLE 8 o-GLA-ACV, ("AK 5")

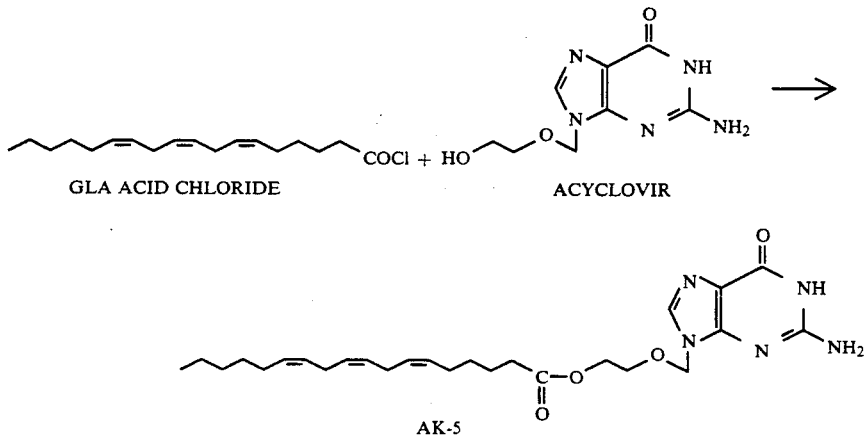

Acyclovir (ACV, 0.5 g, 2.22 mmol, used as a dry white powder) was suspended in anhydrous pyridine (10 ml) and to the mixture stirred under dry nitrogen was added GLA acid chloride (0.788 g, 2.664 mmol). The reaction mixture was stirred overnight at room temperature after which period TLC indicated conversion to the required product. The pyridine was removed in vacuo and the residual syrup was dissolved in chloroform. This was introduced into a column of silica gel (30 g) pre-equilibrated in chloroform:ethanol (30:1, v:v). Elution with chloroform followed by chloroform:ethanol (30:1), (20:1) and finally (15:1), gave the required product, AK-5, as a TLC homogeneous semisolid. Yield, 48% (0.517 g, 1.065 mmol).

EXAMPLE 9 o-LA-ACV, ("AK 6")

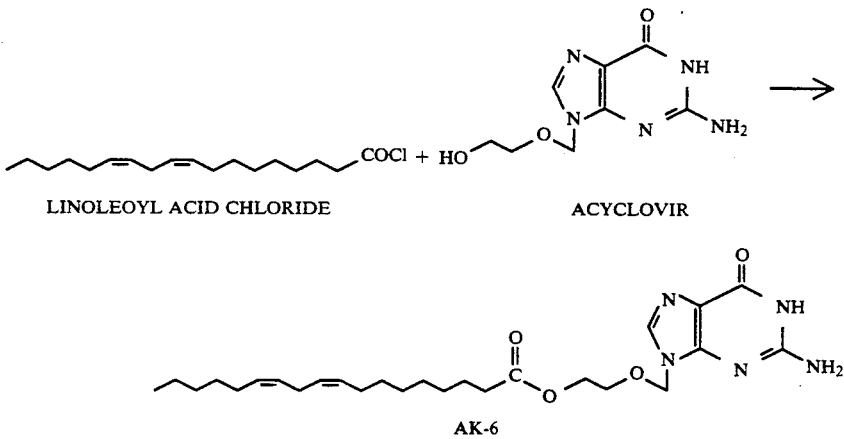

The procedure for this preparation is exactly as above. The quantities used were as follows: ACV, 0.5 g, 2.22 mmol. LA acid chloride, 0.77 g, 2.58 mmol. 10 ml of anhydrous pyridine. Yield 45% (0.487 g, 1.0 mmol).

EXAMPLE 10

Di-GLA-ACV, ("AK 10") (Method B)

Acyclovir (ACV, 0.5 g, 2.22 mmol, used as a dry white powder) was suspended in anhydrous pyridine (10 ml). To the stirred mixture under dry nitrogen was added GLA acid chloride (1.6 g, 5.37 mmol) and 4-dimethyl-amino pyridine (0.061 g, 0.5 mmol). The reaction was stirred overnight at room temperature after which period TLC indicated conversion to the required product. The pyridine was removed in vacuo and the residual syrup was dissolved in chloroform. This was introduced onto a column of silica gel (30 g) preequilibrated in chloroform. Elution with chloroform:petrol (3:1, v:v) followed by chloroform, gave the required product AK-10, as a TLC homogeneous syrup. Yield 58% (0.962 g, 1.20 mmol).

EXAMPLE 11

Di-LA-ACV ("AK 11")

dioxane (2 ml). (The dioxane helps to solublise the starting material). The solution was then cooled to 0° C. and 0.25 ml of NaOH solution (from Aldrich, 30% wt) was added. Stirring was maintained for fifteen minutes at 0° C. after which period TLC indicated complete loss of the starting material and the formation of a slightly lower r.f. product. Dowex ion exchange resin (20 ml, in H+ form) was added and stirring was maintained at room temperature for a further ten minutes. The Dowex was filtered and washed with methanol and the combined filtrate and washings were then evaporated in vacuo to afford the crude product as a pale yellow gum. The gum was dissolved in a minimum of chloroform and applied to column of silica gel (5 g). Elution with chloroform and then chloroform:methanol (20:1) gave the required product as a white solid. The yield was 63% (0.214 g, 0.441 mmol).

EXAMPLE 13 n-LA-ACV ("AK 13")

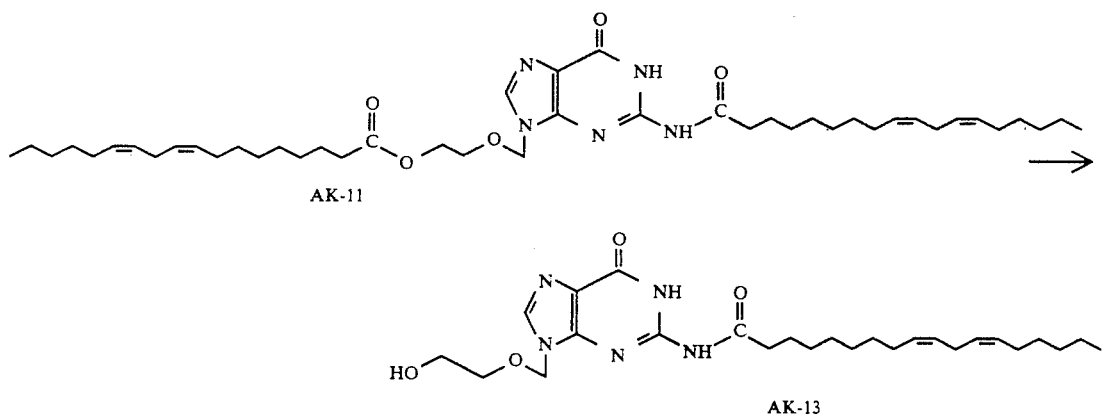

AK-11

The procedure for this preparation is exactly as above. The quantities used were as follows: ACV 0.5 g, 2.22 mmol. LA acid chloride, 1.5 g, 5.1 mmol. 10 ml of anhydrous pyridine. Yield 60% (1.001 g, 1.332 mmol).

EXAMPLE 12 n-GLA-ACV ("AK 12")

AK-13

The procedure for this synthesis is exactly as above. The quantities used were as follows: AK-11, 0.786 g, 1.100 mmol and 0.30 ml of NaOMe solution. The yield of AK-13 after chromatography was 61% (0.326 g, 0.67 mmol).

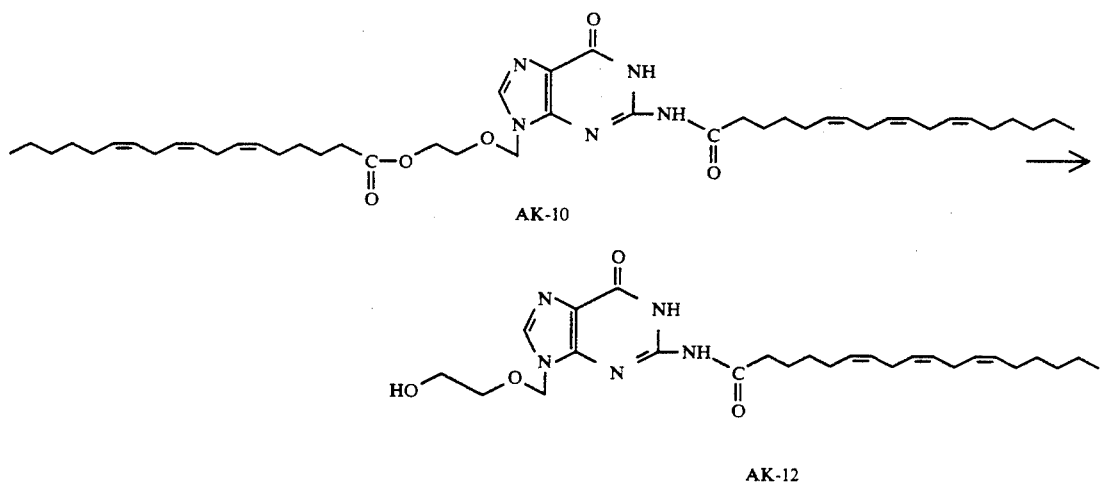

AK-10

AK-12

A sample of AK-10 (0.520 g, 0.698 mmol) was dissolved in anhydrous methanol (10 ml) and anhydrous

EXAMPLE 14

GLA-D4T ("AK 14")

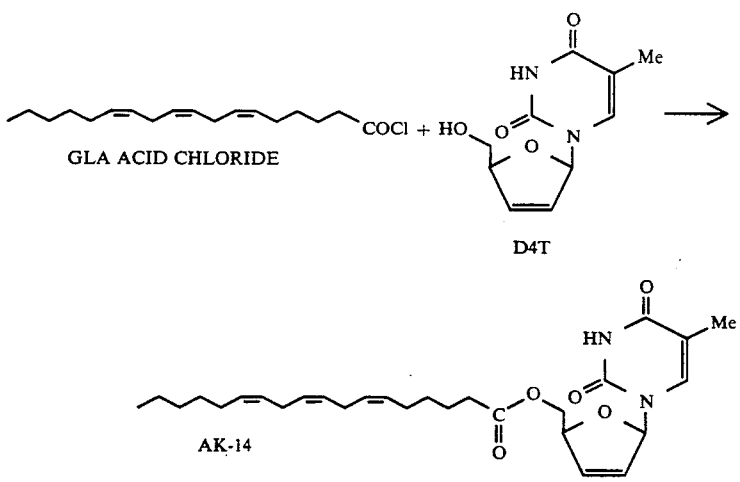

A solution of dideoxy-didehydro thymidine (0.420 g, 1.910 mmol) in anhydrous pyridine (8 ml) was cooled to 0° C. and to this solution was added GLA acid chloride (1.138 g, 3.818 mmol). The solution was stirred overnight under an atmosphere of dry nitrogen after which period TLC indicated complete loss of the starting material. The pyridine was removed in vacuo and the residual syrup was dissolved in chloroform:petrol (2:1). This was then introduced onto a column of silica gel (20 g) pre-equilibrated in chloroform:petrol (2:1). Elution with chloroform:petrol (2:1), (3:1) and finally chloroform gave the required product as a TLC homogeneous syrup. Yield 59% (0.542 g, 1.13 mmol).

EXAMPLE 15

LA-D4T ("AK 15")

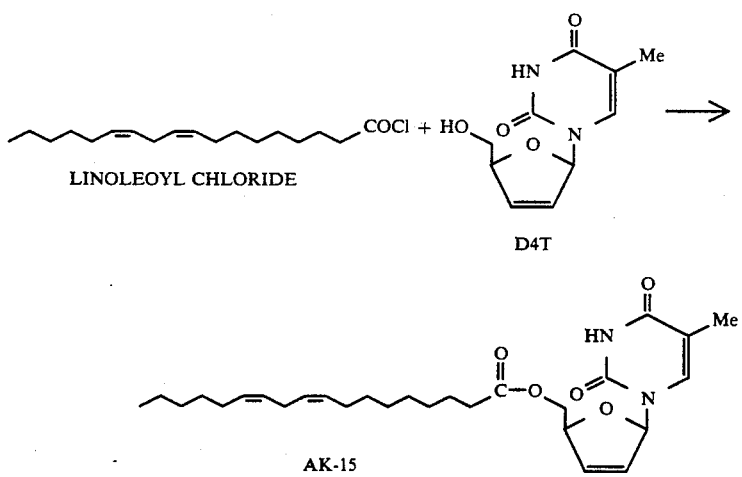

The procedure for this synthesis is exactly as above. The quantities used were as follows: D4T, 0.380 g, 1.727 mmol and linoleoyl chloride (1.033 g, 3.45 mmol) in anhydrous pyridine (10 ml). The yield after chromatography was 53% (0.442 g, 0.92 mmol).

The following synthesis examples are given in abbreviated form using the same methods but with different starting bases. They are written out as for LA derivatives but other n-6 series derivatives such as those of GLA in particular, and n-9, n-7 and n-3 series derivatives are all, as with Examples 1 to 15, made simply by using the acid chlorides of the desired acids instead of those of LA and GLA expressly set out.

EXAMPLE 16 o-LA-ddC "NL 1"

The procedure for this synthesis corresponds to that for AK2 but with use of ddC; a conventional protecting group is first added to the amino position of the base to restrict subsequent reaction with the linoleoyl acid chloride to the 5'-hydroxy group. After formation of the ester linkage the protecting group is removed leaving the title compound ("o" indicates attachment of the fatty acyl group at an oxygen atom, that of the 5'-hydroxy group).

EXAMPLE 17 n-LA-ddC "NL 2"

The procedure for this synthesis again corresponds to that for AK2; no amino protecting group being used however. Since the amino position on the pyrimidine ring is more reactive than the hydroxy position the first acyl compound to form will be the n-LA-ddC (amide linkage, "n" indicating attachment of the fatty acyl group of a nitrogen atom, that of the heterocycle amino group).

EXAMPLE 18 di-LA-ddC "NL 3"

The procedure for this synthesis is as above but carried to completion. Both reactive sites (hydroxyl and amine) react with the linoleoyl acid chloride.

EXAMPLE 19 o-LA-ddA "NL 4"

The procedure for this synthesis is the same as that for NL1 except that ddA is used as the substrate base.

EXAMPLE 20 n-LA-ddA "NL 5"

The procedure for this synthesis is the same as that for NL2 except that ddA is used as the substrate base.

EXAMPLE 21 di-LA-ddA "NL 6"

The preparation of this material is the same as that for NL3 except that ddA is used as the substrate base.

EXAMPLE 22 n-LA-DHPG "NL 7"

The preparation of this material is the same as AK13 except that gancyclovir is used in place of acyclovir. Initial reaction conditions result in both ester and amide linkages being formed as in the preparation of NL8, but ester bonds are subsequently broken by hydrolysis in alkaline conditions.

EXAMPLE 23 tri-LA-DHPG "NL 8" (two ester linkages, one amide).

The preparation of this material corresponds to the preparation of AK11.

EXAMPLE 24 o-di-LA-DHPG "NL 9"

The preparation of this material corresponds to the preparation of AK6.

EXAMPLES OF FORMULATIONS

The following examples of formulations illustrate the therapeutic application of the invention, in formulations which as to the mode of formulation per se are conventional as follows:

| a. Syrup of suspension | |
|---|---|
| active ingredient | 0.25 g |
| sorbitol solution | 1.5 g |
| glycerol | 0.005 g |
| dispersible cellulose | 0.005 g |
| sodium benzoate | 0.010 ml |
| water | 5 liter |

Mix the sorbitol and glycerol with part of the water. Dissolve the sodium benzoate in water and add to the bulk, then add and disperse the cellulose and active ingredient. Make up to volume.

| b. Suppository | |
|---|---|
| | mg/suppository |
| active ingredient | 250 |
| hard fat, BP (Witepsol H15-Dynamit Nobel (trade mark)) | 1770 |
| | 2020 |

One-fifth of the Witepsol H15 is melted at 45° C. and the active ingredient added to the molten base with mixing. The remaining Witepsol H15 is added and stirred to a homogenous mix. The entire suspension is passed through a 250 μm stainless steel screen, cooled to 38° C. to 40° C. and filled into plastic moulds.

Administration by suppository gives access to the bloodstream without passage through the portal vein to the liver, where glucuronidation and other processes causing loss of active drug primarily occur.

| c. Pessaries | |
|---|---|
| | mg/pessary |
| active ingredient | 250 |
| anhydrous dextrose | 380 |
| potato starch | 363 |
| magnesium stearate | 7 |
| | 1000 |

The above ingredients are mixed directly and pessaries prepared by direct compression of the resulting mixture.

Pessaries like the formulations at d), e) and j) are an example of topical formulations, showing the advantageous percutaneous absorption properties given by the fat-compatible nature of the derivatives of the invention.

| d. Cream | |
|---|---|
| | weight (g) |
| active ingredient | 5.0 |
| glycerol | 2.0 |
| cetostearyl alcohol | 6.8 |
| sodium lauryl sulphate | 0.8 |
| white soft paraffin | 12.5 |
| liquid paraffin | 5.0 |
| chlorocresol | 0.1 |
| purified water | 100.00 |

The active compounds are dissolved in a mixture of purified water and glycerol and heated to 70° C. The remaining ingredients are heated together at 70° C. The two parts are added together and emulsified. The mixture is cooled and filled into containers.

| e. Ointment | |
|---|---|
| | weight (g) |
| active ingredient | 12 |
| white soft paraffin | 88 |
| | 100 |

The white soft paraffin is melted at 60° C. The active ingredient is added and dispersed, allowed to cool, and filled into collapsible metal tubes.

f. Injection

| | weight |
|---|---|
| active ingredient | 250 mg |
| intralipid (Kabi-Vitrium) | 10 ml |

This composition is for example useful for intravenous injection.

g. Tablet

| | mg/tablet |
|---|---|
| active ingredient | 100 |
| lactose | 235 |
| starch | 50 |
| polyvinylpyrrolidone | 50 |
| magnesium stearate | 5 |
| | 500 |

Mix the active compound with the lactose and starch and wet granulate with a solution of the polyvinyl-pyrrolidone. Dry, sift, blend the granules with magnesium stearate and compress.

These formulations g), h) and i) are examples of those where the lipid compatibility of the derivatives of the invention leads to uptake in part direct into the lymph system with the advantage of avoiding direct passage to the liver already referred to.

h. Capsule (I)

| | mg/capsule |
|---|---|
| active compound | 200 |
| lactose | 189 |
| sodium starch glycollate | 8 |
| polyvinylpyrrolidone | 6 |
| magnesium stearate | 2 |
| | 400 |

Mix the active compound with the lactose and sodium starch glycollate and wet granule with a solution of the polyvinylpyrrolidone. Dry, sift, blend the granulate with the magnesium stearate and fill into hard gelatin capsules.

i. Capsule (II)

| | mg/capsule |
|---|---|
| active ingredient | 100 |
| arachis oil | 500 ml |

The active compound is dissolved in arachis oil and filled into soft or hard gelatin capsules.

Arachis oil compositions are for example useful against ocular herpes infection.

j. Topical preparation (liquid)

| | |
|---|---|
| active ingredient | 0.5% |
| propylene glycol | 50.0% |
| ethanol | 49.5% |

The following are specific examples employing the above formulations:

Example (1) Tablets containing 300 mg of GLA-AZT. 1 or 2 tablets to be taken 4 to 6 hourly against herpes simplex or HIV and related retroviral infections.

Example (2) Tablets as in Example (1) but prepared using the EPA or arachidonic acid derivative of AZT.

Example (3) Hard gelatin capsules containing 150 mg of GLA-AZT. 1 or 2 capsules to be taken 4 to 6 hourly against herpes simplex or retroviral infections.

Example (4) Syrup for oral administration containing 150 mg/ 5 ml GLA-AZT. 5 ml to be taken 4 to 6 hourly against herpes simplex or retroviral infections.

Example (5) Solution for oral administration or intramuscular or intravenous injection containing 200 mg of GLA-AZT in 3 ml, to be given 4 to 6 hourly against herpes simplex or retroviral infections. Intravenous injection for rexample is a preferred route for achieving therapeutic concentration in brain tissue across the blood brain barrier.

Example (6) Ointment or cream for topical administration against herpes simplex, containing 2% by weight GLA-AZT. It may be applied to a human afflicted with a herpetic lesion at the afflicted sites at a rate of 1 to 5 mg/cm$^2$ three times daily for a period of one week. Reduction in the size of the lesion is noted after three days.

Examples (7) to (18) Correspondingly, GLA-AHT, or either LA-AHT or LA-AZT, are used individually in amounts and formulations as above. Further alternatives are corresponding preparations based on the ddC, ddA and D4T derivatives of synthesis examples 14 to 21, namely AK14 and 15 and NL1 to 6, for the same formulations and uses.

Example (19) Hard gelatin capsules containing 800 mg of GLA-AZT. 1 or 2 capsules to be taken 4 to 6 hourly against herpes zoster.

Example (20) Tablets containing 300 mg of di-GLA-acyclovir or o-GLA-acyclovir (synthesis Examples (7) and (8)); 1 or 2 tablets to be taken 4 to 6 hourly against virus infections. The n-GLA-acyclovir of synthesis Example 11 is an alternative.

Example (21) Tablets as in Example (20) but prepared using the corresponding LA, EPA or arachidonic acid derivatives of acyclovir.

Example (22) Hard gelatin capsules containing 150 mg of the o-GLA-acyclovir or other derivatives; 1 or 2 capsules to be taken 4 to 6 hourly against virus infections.

Example (23) Syrup for oral administration containing 150 mg/5 ml of the o-GLA-acyclovir or other derivatives; 5 ml to be taken 4 to 6 hourly against virus infections.

Example (24) Ointment or cream for topical administration against virus infections containing 2% by weight of the o-GLA-acyclovir or other derivatives.

Examples (25) to (29) Correspondingly, DHPG (gancyclovir) derivatives are used as set out in Examples (22) to (24).

Among the virus infections for which the above formulations (20) to (29) may be used are herpes simplex and herpes zoster.

PHYSICAL PROPERTIES

Physical properties of certain of the new compounds have been measured as follows:

TABLE 3

| | Partition co-efficients, water/chloroform | |
|---|---|---|
| Compound | | % in chloroform phase |
| AK 1 | GLA—AZT | >99% |
| AK 2 | LA—AZT | >99% |
| AK 3 | GLA—AHT | >98% |

TABLE 3-continued

| Compound | Partition co-efficients, water/chloroform | % in chloroform phase |
|---|---|---|
| AK 4 | LA—AHT | >99% |
| AK 5 | GLA—ACV | >99% |
| AK 6 | LA—ACV | >99% |
| AK 7 | AZT (comparative) | 15% |
| AK 8 | AHT (comparative) | 4% |
| AK 9 | ACV (comparative) | 1% |
| AK 10 | di-GLA—ACV | >99% |
| AK 11 | di-GLA—ACV | >99% |

TABLE 4

| | Absolute Solubilities | |
|---|---|---|
| | In water | In $CHCl_3$* |
| AK 5 GLA—ACV | 0.028 g/l | >50 g/l |
| AK 6 LA—ACV | 0.014 G/L | >50 g/l |
| AK 9 ACV | 1.590 g/L | 0.006 g/l |

*98 to 99% pure, with 1% balance ethanol to stabilise.

As already discussed, the greatly enhanced solubility in chloroform of the fatty acid-ACV compounds compared to ACV itself, with comparable Figures shown by AZT/AHT, is important to the drug pharmacokinetics. Lipophilic compounds pass through cell membranes to act within the cytoplasm. Normally, water soluble compounds do not readily pass through cell membranes and require specific membrane transport mechanisms to achieve high intra-cellular concentrations. Further, the oil like properties of the fatty acid nucleoside analogue derivatives itself assists manufacture, formulation, and application (especially topically) for anti-viral formulations.

TESTING FOR EFFICACY

A. Inhibition of Virus Replication, Method

1. Mono-layers of baby hamster kidney cells (BHK-21) are prepared in Petri dishes containing ETC medium (Eagle's minimal essential medium +10% tryptose phosphate broth +10% new born calf serum).

2. After incubation the medium is poured off to leave the layer of cells attached to the Petri dish. A solution containing virus, specifically herpes simplex virus Type I (HSV I) for example, in ETC medium is then added to the dish and incubated with intermittent rocking for one hour to allow the virus to adsorb to the cells of the mono-layer. Unadsorbed virus is then removed by pouring off the virus-containing medium and washing twice with new sterile medium. Then new medium is added to each Petri dish. At this stage various concentrations of drug can be added to the medium.

3. After a further 24 hour incubation to allow the virus to multiply in the cells to which it has become adsorbed, the cultures are treated to enable the amount of virus produced to be assayed. First the dishes are frozen to −70° C. and thawed to disrupt the mono-layer and break up the cells. Then the medium and the disrupted cells are transferred to bijou bottles and sonicated to break down the cells completely and to release all the virus particles the cells contain. The sonicated medium is then diluted with fresh sterile ETC medium to give concentrations of the original Petri dish fluid of $10^{-2}$, $10^{-4}$, $10^{-6}$ and $10^{-8}$.

4. The number of virus particles (plaque forming units) in the dilutions is then assayed. A standard number of BHK cells (usually $8 \times 10^6$) is added to 2 ml of the diluted solutions and incubated for one hour, with cautious, gentle shaking, and 8 ml of Eagle's minimal essential medium +2% new born calf serum + carboxymethyl cellulose is then added to the cell suspension. This medium has gelling properties which prevent spreading of the virus through the medium and which encourage the formation of discrete plaques in cell mono-layers. The medium from each dilution is then dispensed into Petri dishes and incubated for two to three days.

5. The number of plaques formed is then counted and the amount of active virus expressed as the number of plaque forming units (pfus) as follows. The medium is poured off and the cell mono-layer is fixed using 10% formol saline and stained with dilute carbol fuchsin. The number of plaques in each Petri dish is counted. Based on the dilutions, the number of plaque forming virus particles in the original solutions is calculated.

B. Inactivation of Virus, Method

1. A virus solution containing $2 \times 10^5$ pfu/ml is prepared in phosphate buffered saline (Dulbecco's A).

2. The compound to be tested is made up in Dulbecco's medium A in a suitable range of dilutions.

3. Equal volumes of the virus and drug solution are mixed together. Control solutions without drug are also used.

4. The virus and drug are incubated for an appropriate period of time, in this example, thirty minutes.

5. The numbers of active viral particles in the solution are assayed as in items 4 and 5 under A.

C. Results, AZT and AHT

AZT alone is known to have no effect as regards either the replication or the inactivation of herpes simplex virus, see for example, E. de Klerk et al, Biochemical Pharmacology 29: 1849, (1980) and the same is true of AHT. The inventors have, however, investigated the effects of GLA in the form of its alcohol, of LA, and of GLA-AZT and GLA-AHT and corresponding LA compounds, prepared as described herein, on herpes simplex, Type 1, Troisbel strain.

A first investigation was an assay to test whether GLA-AZT or GLA alcohol could inhibit viral replication and was set up using the method above. GLA alcohol was found to have no effect at all. The effects of GLA-AZT are given below (Table 5). In the Table, the figures are the concentration of viral particles in pfu/ml present in the cells + medium at the end of the replication stage (3).

TABLE 5

| Inhibition of Replication | | |
|---|---|---|
| GLA—AZT concentration | | |
| μg/ml | Molar | Viral titre (pfu/ml) |
| 0 | 0 | $9.0 \times 10^8$ |
| 25 | $47.5 \times 10^{-6}$ | $1.02 \times 10^8$ |
| 50 | $95.0 \times 10^{-6}$ | $<1.0 \times 10^2$ |

The figures demonstrate that in complete contrast to either AZT alone or GLA alcohol alone, the compound of GLA-AZT was able to inhibit viral replication effectively. The new compound thus revealed properties possessed by neither of its constituents, inhibition of herpes virus replication. Like results are obtained when AHT or LA compounds are tested.

A second investigation was an assay to test whether GLA-AZT and GLA alcohol inactivated the herpes virus. The results are shown below (Table 6). In the Table, the figures are concentrations of viral particles present after incubation of the virus for 30 minutes with solutions of the drugs.

TABLE 6

| μg/ml | Inactivation of Virus | | Virus titre |
|---|---|---|---|
| | Molar | | |
| (a) GLA-alcohol | | | |
| 0 | 0 | | $5.4 \times 10^4$ |
| 5 | $18 \times 10^{-6}$ | | $3.0 \times 10^3$ |
| 10 | $36 \times 10^{-6}$ | | $2.2 \times 10^2$ |
| 25 | $90 \times 10^{-6}$ | | $<1.0 \times 10^2$ |
| (b) GLA—AZT | | | |
| 0 | 0 | | $4.5 \times 10^4$ |
| 5 | $9.5 \times 10^{-6}$ | | $2.7 \times 10^3$ |
| 10 | $19 \times 10^{-6}$ | | $<1.0 \times 10^{-2}$ |
| 25 | $48 \times 10^{-6}$ | | $<1.0 \times 10^2$ |

The figures demonstrate that both GLA alcohol and the GLA-AZT are able to inactivate the herpes simplex virus but the GLA-AZT was more effective. Similarly LA was active at concentrations comparable to GLA, and LA-AZT at 1 to 3 μg/ml, with corresponding results for AHT derivatives. Other viricidal fatty acids may, it follows, be expected to retain their activity when used as derivatives.

In summary, AZT and AHT alone have no effect on either inactivation or replication of simplex herpes I virus, and while GLA alone and other acids such as LA have same effect in inactivating the herpes virus they are completely unable to inhibit viral replication. In contrast, compounds such as AZT-GLA and AZT-LA and the corresponding AHT derivatives are able both to inactivate the herpes virus and to inhibit its replication. The latter effect, in particular, could not have been predicted on the basis of the known separate effects of the two agents.

D. Results, ACV and materials generally

Using the above methods the results summarised in the following Table have been obtained in relation to ACA and derivatives thereof and also in relation to AZT and AHT.

TABLE 7

ANTIVIRAL ACTIVITY OF COMPOUNDS AGAINST HERPES SIMPLEX VIRUS I

| COMPOUND | INACTIVATION OF VIRUS ($\log_{10}$ reduction in virus titre) | INHIBITION OF VIRAL REPLICATION ($\log_{10}$ reduction in virus titre) |
|---|---|---|
| AK 1 | 1.0 @ 1 mg/l | no inhibition up to 100 mg/l |
| GLA—AZT | 2.0 @ 5 mg/l | |
| AK 2 | 2.2 @ 1 mg/l | no inhibition up to 100 mg/l |
| LA—AZT | 2.8 @ 5 mg/l | |
| AK 3 | 1.6 @ 0.5 mg/l | 0.5 @ 25 mg/l |
| GLA—AHT | 2.7 @ 1.0 mg/l | 0.9 @ 50 mg/l |
| | | 1.2 @ 100 mg/l |
| AK 4 | 2.75 @ 1 mg/l | no inhibition up to 100 mg/l |
| LA—AHT | 2.9 @ 5 mg/l | |
| AK 5 | no inactivation up to 50 mg/l | 1 @ 0.1 mg/l |
| GLA—ACV | | 2.2 @ 0.5 mg/l |
| AK 6 | no inactivation up to 50 mg/l | 2.4 @ 1 mg/l |
| LA—ACV | | 4.2 @ 5 mg/l |
| AK 7 | no inactivation up to 50 mg/l | No inhibition up to 100 mg/l |
| AZT | | |
| AK 8 | no inactivation at 10 mg/l | no inhibition of replication |
| AHT | 0.7 @ 25 mg/l | |
| AK 9 | no inactivation up to | 2 @ 0.1 mg/l |

TABLE 7-continued

ANTIVIRAL ACTIVITY OF COMPOUNDS AGAINST HERPES SIMPLEX VIRUS I

| COMPOUND | INACTIVATION OF VIRUS ($\log_{10}$ reduction in virus titre) | INHIBITION OF VIRAL REPLICATION ($\log_{10}$ reduction in virus titre) |
|---|---|---|
| ACV | 50 mg/l | 2.3 @ 0.5 mg/l |
| AK 10 | 0.94 @ 1 mg/l | 0.45 @ 0.1 mg/l |
| di-GLA—ACV | 1.54 @ 5 mg/l | 0.86 @ 0.5 mg/l |
| | | 1.13 @ 1.0 mg/l |
| AK 11 | 0.15 @ 1 mg/l | 1.69 @ 1 mg/l |
| di-LA—ACV | 1.55 @ 5 mg/l | 2.46 @ 5 mg/l |
| AK12 | 0.6 @ 1 mg/L | 1.9 @ 0.1 mg/L |
| n-GLA—ACV | 1.4 @ 5 mg/L | 3.9 @ 1 mg/L |
| AK13 | 1.3 @ 1 mg/L | 2.45 @ 0.1 mg/L |
| n-LA—ACV | 1.8 @ 5 mg/L | 4.3 @ 1 mg/L |

Anti-HIV activity assay

Results in relation to HIV virus were obtained by the method of Pauwels et al, Journal of Virological Methods 20, 309 to 321 (1988), as follows:

Method

MT-4 cells ($2.5 \times 10^4$/well) were infected with HIV (100 $CCID_{50}$) and incubated in the presence of varying concentrations of the test compounds (added immediately after virus infection). After five days incubation at 37° C. in a $CO_2$ incubator, the number of viable cells was assessed by the MTT (tetrazolium) method. Antiviral activity and cytotoxicity of the compounds are expressed as $ED_{50}$ (50% effective dose) and $CD_{50}$ (50% cytotoxic dose), respectively. SI (selectivity index = $CD_{50}/ED_{50}$.

Results

These are given in Table 8 and Table 9 below in relation to $HTLV-III_B$ and $LAV-2_{ROD}$ viruses.

TABLE 8

Results: $HTLV-III_B$

| | $CD_{50}$ (μg/ml) | $ED_{50}$ (μg/ml) | Selectivity index (SI) |
|---|---|---|---|
| AK 1 | 6.0270 | 0.000754 | 7993 |
| AK 2 | 9.4929 | 0.000365 | 26008 |
| AK 3 | 17.7480 | >40 | <1 |
| AK 4 | 18.1641 | >40 | <1 |
| AK 5 | 17.2134 | >40 | <1 |
| AK 6 | 30.7272 | >40 | <1 |
| AK 7 | 1.5368 | 0.000372 | 4131 |
| AK 8 | 771.20 | 13.10 | 59 |
| AK 9 | 300.0550 | >1000 | <1 |
| AK 10 | 4.4160 | >8 | <1 |
| AK 11 | 13.0923 | >40 | <1 |
| AK 14 | 10.26 | 0.076 | 134 |
| AK 15 | 16.50 | 0.064 | 256 |
| AK 16 (D4T) | 44.41 | 0.077 | 574 |

TABLE 9

Results: $LAV-2_{ROD}$

| | $CD_{50}$ (μg/ml) | $ED_{50}$ (μg/ml) | Selectivity index (SI) |
|---|---|---|---|
| AK 1 | 8.3825 | 0.000858 | 9770 |
| AK 2 | 5.9512 | 0.000744 | 7999 |
| AK 3 | 16.8593 | >40 | <1 |
| AK 4 | 17.4332 | >40 | <1 |
| AK 5 | 18.7751 | >40 | <1 |
| AK 6 | 62.4323 | >100 | <1 |
| AK 7 | 1.5633 | 0.00053 | 2928 |
| AK 8 | 330.40 | 21.80 | 15 |
| AK 9 | 397.5805 | >10000 | <1 |
| AK 10 | 11.4641 | >40 | <1 |

TABLE 9-continued

| | Results: LAV-2$_{ROD}$ | | |
|---|---|---|---|
| | CD$_{50}$ (μg/ml) | ED$_{50}$ (μg/ml) | Selectivity index (SI) |
| AK 11 | 10.1674 | >40 | <1 |
| AK 14 | 8.84 | 0.080 | 110 |
| AK 15 | 24.23 | 0.064 | 378 |
| AK 16 (D4T) | 46.65 | 0.039 | 1196 |

We claim:

1. An anti-viral compound having a long chain fatty acyl group attached to a nucleoside or nucleoside analogue which nucleoside or nucleoside analogue comprises a sugar/sugar analogue, the fatty acyl group being attached directly to a hydroxy group or to an amino group of the sugar/sugar analogue or heterocyclic moiety of the nucleoside or nucleoside analogue, wherein the long chain fatty acyl group is selected from the group consisting of fatty acids of the n-9 series having at least 20 carbon atoms, fatty acids of the n-7 and n-6 series having at least 18 carbon atoms, each said fatty acyl group having at least 3 unsaturations, and fatty acids of the n-3 series having at least 18 carbon atoms and having at least 4 unsaturations.

2. A fatty acyl AZT ester according to claim 1.

3. A fatty acyl acyclovir ester, amide or ester/amide according to claim 1.

4. A fatty acyl ddC, ddA, D4T or gancyclovir derivative according to claim 1.

5. A pharmaceutical composition for enhancing the transport of anti-virals comprising the anti-viral of claim 1, together with a pharmaceutically acceptable carrier or diluent.

6. A pharmaceutical composition for enhancing the transport of necleoside analog anti-virals comprising the pentose nucleoside derivatives of claim 1, together with a pharmaceutically acceptable carrier or diluent.

7. A method of enhancing the transport of an anti-viral across lipid barriers in the body or of inhibiting glucuoronidation reducing drug efficacy in the treatment of viral infections, wherein there is administered to a person requiring same an effective amount of a compound according to claim 1.

8. A method of enhancing transport of an anti-viral across lipid barriers in the body, wherein there is administered to a person requiring same an effective amount of a compound according to claim 4.

9. A compound having a long chain fatty acyl group attached to a pentose nucleoside, or of an analogue thereof having an acyclic group in place of the pentose which acyclic group has a hydroxy substituted carbon at the position corresponding to the 5' position of the pentose, said fatty acid group being an ester attached at the 5' position of the nucleoside or the hydroxy substituted carbon wherein the long chain fatty acyl group is selected from the group consisting of fatty acids of the n-9 series having at least 20 carbon atoms, fatty acids of the n-7 and n-6 series having at least 18 carbon atoms, each said fatty acyl group having at least 3 unsaturations, and fatty acids of the n-3 series having at least 18 carbon atoms and having at least 4 unsaturations.

10. A fatty acyl AZT or AHT ester according to claim 9.

11. A fatty acyl acyclovir ester, amide or ester/amide according to claim 9.

12. A fatty acyl ddC, ddA, D4T or gancyclovir derivative according to claim 9.

13. A method of enhancing transport of nucleoside analogue anti-virals across lipid barriers in the body, or of inhibiting glucuronidation reducing drug efficacy in the treatment of viral infections, without loss of replication inhibiting activity, wherein there is administered to a person requiring same an effective amount of a compound according to claim 9.

14. A method of enhancing transport of nucleoside analogue anti-virals across lipid barriers in the body or of inhibiting glucuronidation reducing drug efficacy, in the treatment of viral infections, without loss of replication inhibiting activity, wherein there is administered to a person requiring same an effective amount of a compound according to claim 12.

15. A method treating a herpes virus infection, comprising administering to a sufferer therefrom an effective amount of a compound having a long chain fatty acyl group attached by an amino or hydroxy group of the sugar/sugar analogue or heterocyclic moiety to AZT, AHT, ddC, ddA or D4T wherein the long chain fatty acyl group is selected from the group consisting of fatty acids of the n-9 series having at least 20 carbon atoms, fatty acids of the n-7 and n-6 series having at least 18 carbon atoms, each said fatty acyl group having at least 3 unsaturations, and fatty acids of the n-3 series having at least 18 carbon atoms and having at least 4 unsaturations.

16. A method treating a virus infection comprising administering to a sufferer therefrom an effective amount of an acyclovir or gancyclovir derivative having a long chain fatty acyl group attached to an amino or hydroxy group of the sugar/sugar analogue or heterocylic moiety thereof, wherein the long chain fatty acyl group is selected from the group consisting of fatty acids of the n-9 series having at least 20 carbon atoms, fatty acids of the n-7 and n-6 series having at least 18 carbon atoms, each said fatty acyl group having at lest 3 unsaturations, and fatty acids of the n-3 series having at least 18 carbon atoms and having at least 4 unsaturations.

17. The method of claim 15, wherein the virus infection is herpes simplex or herpes zoster.

18. A pharmaceutical composition for the treatment of a herpes virus infection comprising a compound having a long chain fatty acyl group attached directly to a hydroxy group or to an amino group of the sugar/sugar analogue or heterocyclic moiety of AZT, AHT, ddC, ddA or D4T, wherein the long chain fatty acyl group is selected from the group consisting of fatty acids of the n-9 series having at least 20 carbon atoms, fatty acids of the n-7 and n-6 series having at least 18 carbon atoms, each said fatty acyl group having at least 3 unsaturations, and fatty acids of the n-3 series having at least 18 carbon atoms and having at least 4 unsaturations, together with a pharmaceutically acceptable carrier or diluent.

* * * * *